United States Patent [19]

Häberli et al.

[11] 4,208,370
[45] Jun. 17, 1980

[54] PROCESS FOR AGGLOMERATING A SUBSTANCE FROM A LIQUID SYSTEM

[75] Inventors: Roland Häberli, Würenlingen; Hans Mollet, Reinach; Christel Tempel, Riehen, all of Switzerland

[73] Assignee: Ciba-Geigy Corporation, Ardsley, N.Y.

[21] Appl. No.: 892,569

[22] Filed: Apr. 3, 1978

Related U.S. Application Data

[63] Continuation of Ser. No. 737,314, Nov. 1, 1976, abandoned.

[30] Foreign Application Priority Data

Nov. 6, 1975 [CH] Switzerland .................. 14349/75

[51] Int. Cl.$^2$ ............................................ B01J 2/06
[52] U.S. Cl. ............................................ 264/117
[58] Field of Search ........................ 264/9, 117

[56] References Cited

U.S. PATENT DOCUMENTS

| | | | |
|---|---|---|---|
| 3,221,338 | 11/1969 | Segal | 99/93 |
| 3,276,995 | 10/1966 | McDonald, Jr. | 264/117 |
| 3,311,477 | 3/1967 | Segal | 99/113 |
| 3,449,483 | 6/1969 | Quist | 264/117 |
| 3,591,671 | 7/1971 | Burt et al. | 264/117 |
| 3,755,244 | 8/1973 | Hart | 264/117 |
| 3,987,138 | 10/1976 | Hege | 264/117 |

*Primary Examiner*—Donald E. Czaja
*Assistant Examiner*—James R. Hall
*Attorney, Agent, or Firm*—Michael W. Glynn

[57] ABSTRACT

Described is a process for agglomerating a substance from a liquid system with subsequent separation and drying, which liquid system is composed of at least two liquids, which at 20° C. are completely miscible with one another.

23 Claims, No Drawings

PROCESS FOR AGGLOMERATING A SUBSTANCE FROM A LIQUID SYSTEM

This is a continuation of application Ser. No. 737,314 filed on Nov. 1, 1976, now abandoned.

The invention relates to processes for agglomerating a substance from a liquid system; as well as to the agglomerates, as an industrial product, produced by means of these processes; and also to the use of these processes for the isolation of a solid from a suspension.

From DOS No. 2,412,369 is known a process for producing non-dusty, readily wettable and rapidly soluble granulates, in which process the substance to be grandulated is suspended in a liquid not dissolving this substance, and to the suspension is then added a second liquid which wets to dissolves the said substance, and which is immiscible or only partially miscible with the first liquid, and the mixture is maintained in a state of turbulence until agglomerates or granules of the said substance are formed, which are separated and dried.

It has now been further discovered that it is also possible to effect the agglomeration of a substance in two or more liquids which are completely miscible with one another. It has been shown that surprisingly the granulating process in a liquid system of this kind is more rapid and that the granules obtained are more uniform in size than those obtained by the process according to DOS No. 2,412,369. Furthermore, there is the advantage that toxicologically completely safe solvent systems, such as water/ethanol, can be used, a factor which in food technology is of significance in that the granules no longer contain traces of toxicologically inadmissible solvents.

The process according to the invention of agglomerating a substance from a liquid system with subsequent separation and drying is hence characterised in that the liquid system is composed of at least two liquids, which at 20° C. are completely miscible with one another.

The carrying out of the process comprises, for example, suspending a substance, which is to be agglomerated, in a liquid not dissolving this substance, or in a mixture of such liquids; adding to this suspension a second liquid, or a mixture of liquids, which wets or dissolves the said substance and which mixes completely with the suspension liquid; turbulently stirring the mixture until agglomerates of the substance are formed; separating these from the liquid system and drying them.

A preferred procedure for performing the process constitutes a modification of the process, wherein the substance to be agglomerated is continuously added, with stirring, to a liquid system consisting of at least two liquids which at 20° C. completely mix with one another, whereby at least one of the liquids alone wets or dissolves the substance to be agglomerated, in such a manner that agglomerates of the said substance are formed, which are subsequently separated from the system and dried.

The resulting agglomerates are then separated from the liquid system in a known manner, for example by filtration under suction or by normal filtration, and dried by known methods.

The substance to be agglomerated can be a homogeneous substance or a mixture of substances, and can belong to the most varied classes of substances and can be of inorganic or organic nature.

The substances concerned are for example: dyes, pigments, optical brighteners or textile auxiliaries, pharmaceutical products, mixtures of active substances in the manufacture of tablets, pest-control agents, foodstuffs and food supplements such as coffee powder, milk powder or flour; antimicrobics and bacteriostatics; animal feeding stuffs, plant protection products; detergents, paper auxiliaries (e.g. gluing agents), photochemicals, leather chemicals, polymers such as plastics, plastics additives, synthetic resin moulding compounds, explosives, building materials, coal, cres, catalysts, chemicals, fertilisers, intermediates for cement manufacture, starting materials for ceramic products and also raw materials for powder metallurgy.

By dyes as substances are meant here all possible classes, both coloristically and chemically, which are suitable for an aqueous and organic application. Mentioned for example are: basic and cationic dyes, acid dyes, sulphur dyes, vat dyes, mordant dyes, chrome dyes, disperse dyes and direct dyes, whereby the dyes can contain fibre-reactive groups in the molecule. It is understood that also foodstuff dyes and, for example, leather dyes are included.

From a chemical point of view, suitable dyes are, e.g., nitroso, nitro, monoazo, disazo, trisazo, polyazo, stilbene, carotenoid, diphenylmethane, triarylmethane, xanthene, acridine, quinoline, methine, thiazole, indamine, indophenol, azine, oxazine, thiazine, lactone, aminoketone, hydroxyketone, anthraquionone, indigoid and phthalocyanine dyes, as well as 1:1- or 1:2-metal-complex dyes.

Suitable optical brighteners which are used for white tinting belong to all classes of brighteners: they are for example stilbene compounds such as cyanuric derivatives of 4,4'-diaminostilbene-2,2'-disulphonic acid or distyrylbiphenyls, coumarins, benzocoumarins, pyrazines, pyrazolines, oxazines, mono- or dibenzoxazolyl, mono- or dibenzimidazolyl compounds as well as naphthalic acid imides or naphthotriazole and v-triazole derivatives.

By textile auxiliaries are meant chemicals that are required in the processing of the various textile fibres into finished fabrics, such as raw-wool detergents, lubricants, sizing agents, milling agents, impregnating agents, preserving agents, finishing agents, desizing agents, kier-boiling agents, bleaching auxiliaries, dyeing auxiliaries such as dispersing agents and levelling agents, printing auxiliaries, carbonising auxiliaries, mercerising auxiliaries, preparations for producing resistance to creasing and to shrinking, and antistatic preparations.

Pest-control agents are in general known. They are used, e.g., to destroy plant pests (e.g. fungicides, insecticides, acaricides, nematicides, molluscicides and rodenticides), and to prevent plant diseases.

Antimicrobics are antimicrobial substances which are intended to or serve to retard or prevent disadvantageous changes caused by microorganisms in foodstuffs.

Bacteriostatics are substances which inhibit or prevent the growth of bacteria.

By detergents are meant those substances which are composed of, e.g., (a) a surface-active synthetic substance, a washing raw material; (b) a washing auxiliary (detergent additive); (c) special additives such as sodium perborate, magnesium silicate, optical bleaching agents, wetting agents, etc.; and (d) extenders. Both the detergent as such and the individual constituents can be granulated according to the invention.

And, finally, polymers can be granulated, by which are meant macromolecular organic compounds which are obtained by transformation of natural products or by synthesis, and which include also plastic materials.

All these substances, both in the pure or preferably in the commercial form, can be present as dried or moist, aqueous or organic press cake or as a suspension, whereby the liquid on which this press cake or suspension is based can be identical to the suspension liquid or granulating liquid. If the starting material is a suspension, suitable materials are, inter alia, those resulting, for example, after synthesis. A very frequent case is that of aqueous press cakes of water-soluble substances which are precipitated, for example, by salt. Here the water is indeed the suspension liquid, but at the same time it also has the function of the liquid which brings about agglomeration. In order that a controlled agglomeration in this case can occur, there must be added a liquid which does not dissolve the dye but which extracts from the press cake that amount of water which is in excess of that required for the agglomeration process. It serves therefore as the suspension agent during agglomeration.

Liquids which do not dissolve the substance to be agglomerated, i.e. which serve as the suspension liquid, are either water or an organic liquid which satisfy this condition.

A further liquid which wets to dissolves the substance to be agglomerated and which is completely miscible at 20° C. with the suspension liquid is, in the case where the suspension liquid is water, an organic liquid, or a mixture of such liquids, 100% miscible with water at 20° C.; and suitable such organic liquids are, for example, lower aliphatic alcohols such as ethanol, methanol and, in particular, propyl alcohol such as n- and iso-propyl alcohol, or ketones such as acetone. A preferred mixture is water-ethanol and water/n-propyl alcohol.

It is understood that conversely the suspension liquid can be of organic nature and the other liquid can be water.

In the case where the suspension liquid and the other liquid are both of organic nature and satisfy the condition of being 100% miscible with each other at 20° C., suitable organic liquid mixtures are for example: Frigen/isopropanol, Frigen/ethanol, n-butanol/benzene, benzene/n-propanol, ligroin/isopropanol, methanol/formamide, methanol/ethylene dichloride, perchloroethylene/iso- or n-propanol, and propanol/butanol. Particularly good results are obtained however with the following liquid mixtures: Frigen/methanol, toluene/methanol, perchloroethylene/methanol and 1,1,1-trichloroethane/methanol.

The amounts of the individual liquids can vary within wide limits. Ratios of suspension liquid to granulating liquid can vary from 1:99 to 99:1. A preferred ratio is from 30:70 to 80:20, especially 60:40.

It is advantageous if agglomeration occurs in the presence of additional auxiliaries. Such auxiliaries are, for example: binding agents, about 1 to 20% relative to the substance to be agglomerated, diluting agents, about 1 to 1000% relative to the substance to be aggomerated, dispersing agents or surface-active agents, of nonionic, anionic or cationic nature depending on the solid substance, in amounts of 0.1 to 10% relative to the substance to be agglomerated.

In addition to surface-active agents, protective colloids can be added in amounts of up to 20%.

The binding agents serve in particular to increase the mechanical strength of the agglomerates. Such binding agents to be mentioned are, e.g.: polyvinyl alcohol, cellulose derivatives such as carboxymethylcellulose and hydroxypropylcellulose, polyvinylpyrrolidone as well as dextrin.

Suitable diluting agents are, in particular, salts such as alkali salts of inorganic acids, e.g. of hydrochloric acid, sulphuric acid and phosphoric acid, the salts concerned being, e.g., NaCl, $Na_2SO_4$ (Glauber's salt) and phosphate salts.

Good agglomeration results are obtained especially where the process of agglomeration of a substance is performed from a liquid system having at least two liquids completely miscible at 20° C., whereby to this liquid system are added as further auxiliaries, in particular, diluting agents, especially salts. This salt can be already contained in the substance to be agglomerated, or it can be separately added to the liquid system, or it can be present by virtue of the substance itself being of the nature of a salt, e.g. in the case of cationic dyes.

Agglomeration usually occurs at a temperature of about 5° to 100° C., especially 15° to 50° C., in the course of about 10 to 20 minutes.

The agglomerates resulting from the novel processes are of the most varied forms, such as spherical, lenticular, elongated or rod-shaped. The diameter of these forms is about 100 to 1000 microns, and these agglomerates are very uniform in size. Larger agglomerates can however be produced, which can be converted, depending on the stirring duration, even into the form of granules which are over 1000 microns in size.

These agglomerates or granulates have the advantages that compared with the powder form of the corresponding substance, they have a much better wetting property as well as a higher rate of dissolving and more rapid dispersibility, even possessing in certain cases "instant" properties; and also that they are non-dusty. Furthermore, they are very free-flowing and also have a high bulk weight. It is possible in this manner to obtain from soluble substances soluble in water or in an organic medium granulates having "instant" properties, i.e. with immediate breaking down in the solvent. The resulting agglomerates or granulates can in general be dispersed or dissolved easily, and without the use of special stirring devices, in the application medium. Also to be emphasised is the high mechanical stability of the solid granules.

The yield of these granulates can be up to 100%. With the correct choice of liquids, granulation is in most cases complete, with the result that there is a separation of the clear liquid phase from the solid phase of the agglomerates.

A special application for the novel processes is the isolation and drying of solids from a suspension, the procedure being such that, for example, this suspension with at least one further liquid, which wets to dissolves the solids contained in the suspension liquid and which is completely miscible with this liquid, is subjected to a thorough mixing until agglomerates of the solids are formed, which are then separated from the liquid system and optionally dried.

The following Examples illustrate the invention without its scope being limited by them. Temperatures are given in degrees centigrade. In the case of the solvent "Frigen," this is, here and in the following, "FRIGEN 113 TR, corresponding to 1,1,2-trichloro-1,2,2-trifluoroethane."

EXAMPLE 1

33 g of aqueous press cake consisting of 33 percent by weight of the dye from an autocondensation product of p-nitrotoluene-2-sulphonic acid and 67 percent by weight of water is slowly stirred into a paste at 20° with 17 g of n-propyl alcohol. As stirring proceeds there are gradually formed granules which settle out. They are filtered off and dried at 40° in vacuo to give 10 g of dye granulate. This is dustfree and very readily soluble in cold water.

EXAMPLE 2

50 g of the dye according to Example 1 (powder) is suspended in 50 g of n-propyl alcohol with stirring at 20° C. To the suspension is added dropwise 30 ml of water whilst stirring is maintained. After some time, granules are formed which are filtered off and then dried in vacuo at 40°. The resulting product is a dye granulate which is dustfree and which rapidly dissolves in cold water.

It is however also possible to change the addition of the two liquids by mixing 50 g of the same dye with 30 g of water to obtain a thick paste, and to add to this paste, with stirring at 20° C., 50 g of n-propyl alcohol. Granules separate out from the suspension after about 15 minutes as stirring continues. These granules are filtered off and dried at 40° in vacuo.

EXAMPLE 3

20 g of the pulverulent dye of the formula

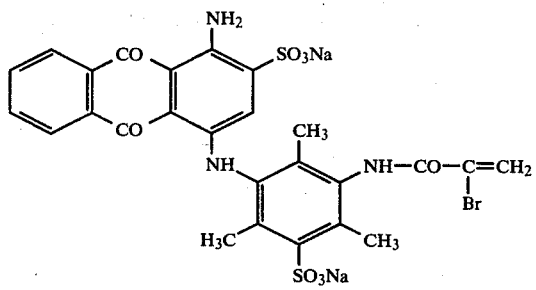

is suspended in 60 g of Frigen. To the suspension is added dropwise at 20°, with stirring, 12.5 ml of methanol. The dye becomes granulated after about 15 minutes. Small granules form which are filtered off and dried at 40°. The product obtained is a dustfree dye granulate which is readily wetted and which dissolves rapidly.

EXAMPLE 4

20 g of the pulverulent dye of the formula

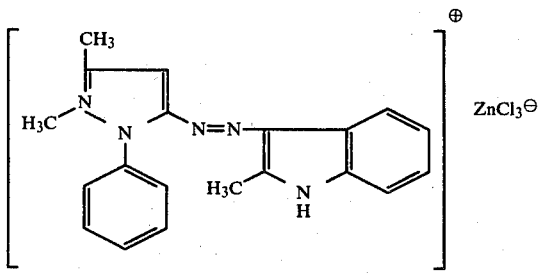

is suspended in 60 g of Frigen at 20°. To this suspension is added dropwise, with stirring, 5 ml of methanol. After 15 minutes' stirring, the dye has become completely granulated. The granules are filtered off and dried at 40° to give a dustfree, easily wettable and readily soluble dye granulate.

EXAMPLE 5

20 g of the pulverulent dye of the formula

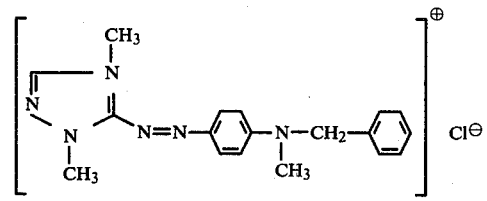

is suspended in 50 g of Frigen at 20°. To the suspension is added 3.5 ml of methanol. Granules are formed which are filtered off and dried at 40°. The resulting product is a dustfree, easily wettable dye granulate.

A dustfree dye granulate is likewise obtained by using, instead of the liquid system Frigen/methanol, identical amounts of the liquid system toluene/methanol, with otherwise the same procedure.

EXAMPLE 6

20 g of the pulverulent dye of the formula

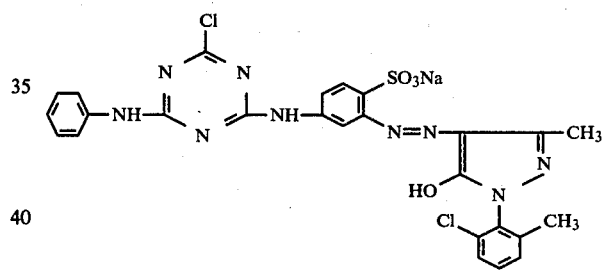

is suspended at 20° in 80 ml of Frigen. To the suspension is added dropwise 30 ml of methanol. Fine granules form immediately and these are filtered off and dried at 40° in vacuo. The granulate is dustfree, readily wettable and rapidly soluble.

The granules can also be produced by mixing the dye into a paste with about 20 ml of methanol, and then suspending this paste, with stirring, in 80 ml of Frigen

EXAMPLE 7

7 g of the dye according to Example 6 is suspended at 20° in 25 g of toluene and to the suspension is added dropwise 10 ml of methanol. After subsequent stirring for a quarter of an hour, the dye has become granulated. The small granules formed are filtered off and dried at 40° in vacuo to give a dustfree dye granulate.

EXAMPLE 8

20 g of the pulverulent dye according to Example 4 is suspended at 20° in 50 g of toluene, and to the suspension is added, with stirring, 7 ml of methanol. Granules are formed, which are filtered off and dried at 40° to give a dustfree dye granulate.

EXAMPLE 9

50 ml of Frigen is mixed at 20° with 7 ml of methanol to give a homogeneous liquid. This mixture is placed into a beaker, and 20 g of the pulverulent dye according to Example 5 is added with stirring. There are formed granules which are filtered off and dried at 50° in vacuo. The product obtained is a dustfree, easily wettable dye granulate.

If 90 ml of Frigen and 10 ml of methanol are used instead of the 50 ml of Frigen and 7 ml of methanol, the result is likewise a good granulation. Conversely, it is also possible to place the dye into the beaker and to then add the mixture of the two liquids.

EXAMPLE 10

60 ml of Frigen is mixed with 5 ml of methanol at 20°. This mixture is placed into a beaker, and 20 g of the pulverulent dye according to Example 4 is added with stirring. Excellent granules are formed spontaneously; these are filtered off and dried at 40°.

EXAMPLE 11

50 ml of perchloroethylene is mixed with 5 ml of methanol at 20°. This mixture is placed into a beaker, and 20 g of the pulverulent dye according to Example 4 is introduced. Granules are formed and are filtered off and then dried at 40°.

EXAMPLE 12

5 g of finely ground coffee is suspended in 45 ml of ethanol. An addition is then slowly made, with turbulent stirring, of 8 ml of an aqueous salt solution (consisting of 8 ml of water and 2 g of sodium chloride). The resulting coffee granules are filtered off and dried. There is thus obtained a coffee granulate which is instantly soluble in cold water.

In the case of certain coffee powders, the moist granules are sticky. This stickiness can be avoided by using for granulation a mixture of the salt solution with ethanol (in the ratio 7:1).

EXAMPLE 13

5 g of finely ground coffee is suspended in 45 ml of isopropanol. An addition is then slowly made, with turbulent stirring, of 6 ml of aqueous sodium chloride solution (20% NaCl). The resulting coffee granules are filtered and dried. There is thus obtained a coffee granulate which is rapidly soluble in cold water.

We claim:

1. In a process for agglomerating a solid substance from a liquid system, separating the agglomerated solid substance from said liquid system and drying the agglomerated substance, the improvement comprising:
   (a) suspending the solid substance to be agglomerated in a first liquid not dissolving said substance,
   (b) adding to the suspension an agglomerating amount of a second liquid which is completely miscible with the first liquid; said second liquid capable of dissolving said solid substance, and
   (c) thoroughly stirring the mixture of said solid substance and first and second liquid until agglomerates of the solid substance are formed in the liquid system.

2. A process according to claim 1, wherein an auxiliary selected from the group consisting of binders, diluting agents, dispersing agents, surface-active agents and protective colloids are added to the liquid system or solid substance to be agglomerated.

3. A process according to claim 2, wherein the auxiliary is an inorganic salt.

4. A process according to claim 1, wherein the solid substance is in the form of an aqueous or organic filter cake.

5. A process according to claim 1, wherein the liquid system consists of water and an organic liquid that is 100% miscible with water at 20° C.

6. A process according to claim 5, wherein the organic liquid is a lower aliphatic alcohol.

7. A process according to claim 6, wherein the lower aliphatic alcohol is ethanol, n-propyl alcohol or isopropyl alcohol.

8. A process according to claim 1, wherein the liquid system consists of organic liquids which are 100% miscible with one another at 20° C.

9. A process according to claim 8, wherein the liquid system used is a 1,1,2-trichlors-1,2,2-trifluoroethane/methanol, toluene/methanol or perchloroethylene/methanol system.

10. A process according to claim 1, wherein the solid substance is organic.

11. A process according to claim 10, wherein the solid substance is a dyestuff.

12. A process according to claim 11, wherein the solid substance is a salt.

13. In a process for agglomerating a solid substance from an organic liquid system, separating the agglomerated solid substance from the liquid system and drying the separated agglomerated solid substance, the improvement comprising continuously adding, with stirring, the solid substance to be agglomerated to an agglomerating amount of a mixture consisting of a first organic liquid which does not dissolve said solid substance, and a second organic liquid which dissolves said solid substance and which is completely miscible with the first liquid, and stirring the solid substance containing liquid system, until agglomerates of said solid substance are formed.

14. A process according to claim 13, wherein an auxiliary selected from the group consisting of binders, diluting agents, dispersing agents, surface-active agents and protective colloids are added to the liquid system or solid substance to the granulated.

15. A process according to claim 13, wherein the liquid system consists of organic liquids which are 100% miscible with one another at 20° C.

16. A process according to claim 15, wherein the liquid system used is a 1,1,2-trichlors-1,2,2-trifluoroethane/methanol, toluene/methanol or perchloroethylene/methanol system.

17. A process according to claim 13, wherein the solid substance is organic.

18. A process according to claim 17, wherein the solid substance is a dyestuff.

19. A process according to claim 18, wherein the solid is a salt.

20. A process for agglomerating a solid substance from an organic liquid system, separating the agglomerated solid substance from the liquid system and drying the separated agglomerated solid substance, the improvement comprising continuously adding, with stirring, an agglomerating amount of a mixture of liquids, at least one of which is organic, and consisting of a first liquid which does not dissolve said solid substance and a second liquid which dissolves said solid substance and which is completely miscible with the first liquid, to said solid substance and stirring the resulting liquid system, until agglomerates of the solid substance are formed.

21. A process according to claim 20, wherein the solid substance is organic.

22. A process according to claim 21, wherein the solid substance is a dyestuff.

23. A process according to claim 22, wherein the solid substance is a salt.

* * * * *